United States Patent [19]
Bradshaw

[11] Patent Number: 5,475,217
[45] Date of Patent: Dec. 12, 1995

[54] ION MOBILITY SPECTROMETRY EQUIPMENT

[75] Inventor: Robert F. D. Bradshaw, Hemel Hempstead, Great Britain

[73] Assignee: Graseby Dynamics Limited, Great Britain

[21] Appl. No.: 211,125

[22] PCT Filed: Sep. 21, 1992

[86] PCT No.: PCT/GB92/01733

§ 371 Date: Mar. 21, 1994

§ 102(e) Date: Mar. 21, 1994

[87] PCT Pub. No.: WO93/06476

PCT Pub. Date: Apr. 1, 1993

[30] Foreign Application Priority Data

Sep. 21, 1991 [GB] United Kingdom ........... 9120192

[51] Int. Cl.$^6$ ........................... H01J 49/40
[52] U.S. Cl. ............... 250/287; 250/289; 250/288
[58] Field of Search ................. 250/287, 288, 250/281, 282, 289

[56] References Cited

U.S. PATENT DOCUMENTS

| | | | |
|---|---|---|---|
| 3,668,382 | 6/1972 | Cohen et al. | 250/287 |
| 4,317,995 | 3/1982 | Bradshaw et al. | 250/288 |
| 5,304,796 | 4/1994 | Siefering et al. | 250/282 |

FOREIGN PATENT DOCUMENTS

| | | |
|---|---|---|
| 0021518 | 7/1981 | European Pat. Off. . |
| 0233579 | 2/1987 | European Pat. Off. . |
| 9010235 | 9/1990 | European Pat. Off. . |
| 2026231 | 1/1980 | United Kingdom ........... 250/281 |

OTHER PUBLICATIONS

PCT Written Opinion (PCT Rule 66).
PCT Notification of Transmittal of the Int'l Search Report on the Declaration.

*Primary Examiner*—Jack I. Berman
*Attorney, Agent, or Firm*—Chan & Christensen

[57] ABSTRACT

Ion Mobility Spectrometry (IMS) equipment comprises an enclosed compartment (10) contained within which there is an IMS cell (12) and a body of absorbent material (14). Samples for detection by the cell (12) are introduced into the compartment (10) by means of a pinhole (30), the samples being drawn in by a negative pressure pulse within the compartment produced by means of a loudspeaker (40). A sample, once it has been drawn in and detected by the cell (12), will diffuse within the compartment (10) and any water vapour or other interfering species thus introduced will be absorbed by the absorbent material (14) so maintaining a clean, dry atmosphere within the device.

15 Claims, 2 Drawing Sheets

ION MOBILITY SPECTROMETRY EQUIPMENT

The present invention relates to ion mobility spectrometry (IMS) equipment.

IMS equipment is increasingly used for the detection and location of gases and vapours of interest in ambient atmosphere. The principles of operation of such equipment are well known in the art and are described, for example, in "Plasma Chromatography" ed. T. W. Carr, Plenum Press (1984).

One disadvantage of the IMS technique is that water vapour and other contaminants present in the equipment can interfere with the detection of many vapours of interest. This has led to the practice of providing a flow of dry clean air within the equipment into which samples are introduced, the dry clean air flow being provided either from an external source, or, in the case of portable equipment, such as the applicants' CAM (RTM) chemical agent monitor, by means of an internal circulatory system including filters and driers. Such a system is described in US Pat. No. 4,317,995.

The need to provide a continuous flow of dry clean air has constrained miniaturisation of IMS equipment as continual operation of an electric fan or pump to maintain airflow in the circulatory loop calls for a power source far larger than would otherwise be necessary and considerably complicates the internal design and the manufacture of the equipment.

It is an object of the invention to at least partly obviate these drawbacks and thereby enable IMS equipment to be further miniaturised.

According to the present invention there is provided IMS equipment comprising a hermetically sealed compartment containing an IMS cell and a body of absorbent material, sample means for introducing a sample into the compartment via an inlet thereof, the IMS cell being arranged to detect or identify gases or vapours of interest present in the sample, water vapour or other interfering species introduced into or otherwise present within the compartment diffusing within the compartment and being absorbed by the body of absorbent material.

The invention also extends to IMS equipment comprising a hermetically sealed compartment containing an IMS cell and a body of absorbent material, into which compartment samples may be introduced to enable the detection or identification of gases or vapours of interest present in such samples, water vapour or other interfering species introduced into or otherwise present in the compartment diffusing within the compartment and being absorbed by the body of absorbent material, whereby a dry clean atmosphere may be maintained within the compartment.

IMS equipment in accordance with the invention, in which there is no requirement for a continuous flow of dry clean air, may be made smaller, simpler, less bulky and more rapidly operable than hitherto.

The invention may be carried into practice in a number of ways, and one specific embodiment will now be described with reference to the accompanying drawings, in which.

Figure 1:
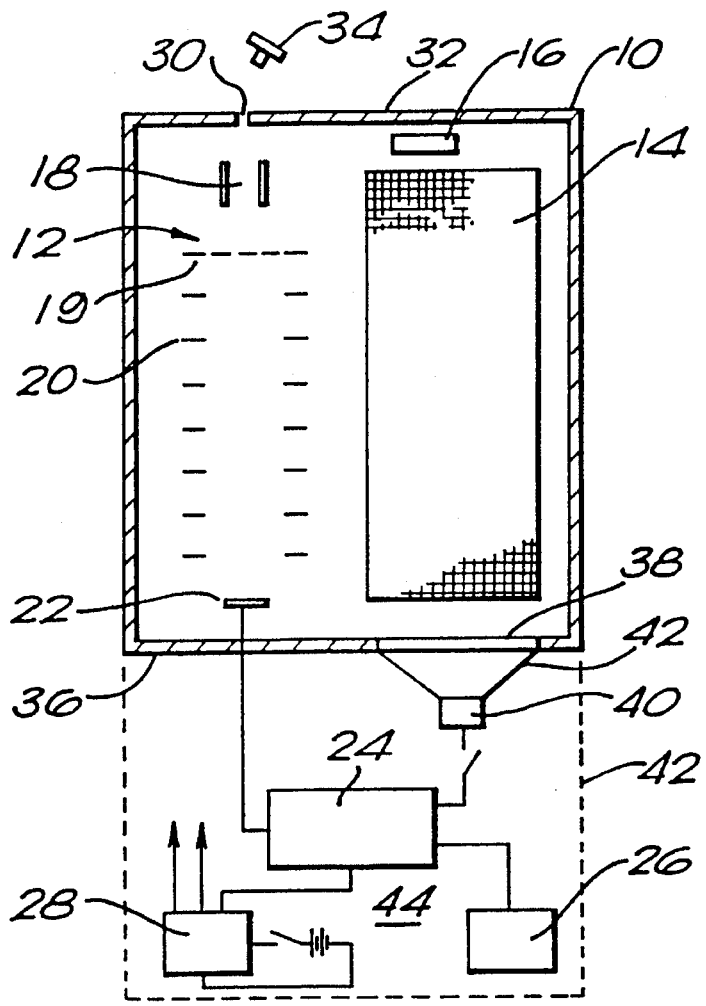
FIG. 1 is a diagrammatic representation of an IMS instrument in accordance with an embodiment of the present invention.

Referring to FIG. 1, IMS equipment (shown here schematically) comprises a sealed case 10, within which is mounted an IMS cell assembly 12, a gauze-faced box 14, containing a body of molecular sieve material, and a dopant permeation source 16.

The IMS cell assembly 12 comprises an ionizing source 18, internally coated with a radioactive source material, typically Nickel-63, to ionise incoming vapour molecules; an electrode structure comprising a gate electrode 19 and a series of electrodes 20, to establish an electrostatic field along the length of the cell 12; and a collector electrode 22, connected to instrument signal processing and control circuitry 24, which in turn is connected, inter alia, to a display or alarm unit 26.

A power supply 28 provides appropriate voltages and currents for the IMS cell 12, and for the processing and control circuitry 24.

The case 10 contains a pin-hole aperture 30 in a wall 32 thereof, directly forward of the ionizing source 18 of the IMS cell 12, with means, here shown as a cap 34, for sealing the aperture 30 when the equipment is not in use.

An end wall 36 of the case 10 has an aperture 38 and carries externally a small moving coil loudspeaker 40 mounted directly over the aperture 38, such that the inner face of a cone 42 is in pneumatic contact with the interior of the case 10; but the aperture is otherwise sealed.

The power supply 28, signal processing and control circuit 24 and display or alarm unit 26 may conveniently be contained in a housing 42, attached to or formed as an extension of the casing 10. The house 42 also serves to protect the loudspeaker 40 and may carry low voltage primary or secondary cells 44 for powering the power supply 28 if the equipment is to be totally self-contained.

In operation, the cap 34 is removed from the aperture 30 and power is applied to the IMS cell 12 and to the signal processing circuit 24 from the power supply 28 driven from the low-voltage cells 44.

Discrete samples of ambient atmosphere possibly containing vapours of interest are drawn into the sealed case 10 through the pin-hole aperture 30 by periodic energisation of the loudspeaker 40, by a suitable drive signal in the manner described in the present applicants' co-pending PCT Patent Application No. PCT/GB92/01259.

If the discrete samples are drawn into the case 10 as single repeated pulses, these slowly diffuse out of the region of the ionizing source (after analysis which happens relatively rapidly). The molecular sieve drying agent, held in the gauze-faced container 14, is able to absorb water-vapour drawn in from the ambient atmosphere sufficiently to maintain a dry internal atmosphere within casing 10 and allow continued IMS detection of water-sensitive species in the samples. Hence, the internal atmosphere will be sufficiently dry, by the time the next sample is taken, to avoid contamination from water vapour that would otherwise still be present in the case from the previous sample.

The brief negative pressure pulse within the casing, provided by the loudspeaker 40, causes the sample to be drawn in in the form of a laminar jet which terminates in an almost stationary vortex ring. The position of the vortex ring depends upon the amplitude and duration of the pressure pulse and on the nature of the hole. It has been found that by suitable adjustment of the length and/or amplitude of the pulse the sample can accurately be deposited at a chosen and controllable distance from the pin-hole aperture 30. Hence, the sample can be arranged to be deposited exactly as required, within the ionizing source 18.

The removal of sample and water vapour from the region of the ionizing source 18 is assisted by an "electric wind" effect in the region of the aperture 30 due to the presence of a body of grounded metal—part of the casing 10—in close proximity to the ionizing source 18, which is in operation held at a potential of about 1 kV.

In practice, after the user of the device removes the plug 34, he simply presses a button (not shown) which actuates the unit. The unit then automatically takes one negative reference reading, one positive reading, then actuates the loudspeaker 40 to inject a sample of ambient gas to be analysed, and subsequently takes a further positive reading and a further negative reading. The unit then automatically subtracts the positive sample reading from the positive background reading, to provide a corrected positive signature for the sample, and similarly subtracts the negative background reading from the negative sample reading to provide a corrected negative sample signature. The negative and positive corrected signatures are stored in computer memory (not shown) and may either be viewed by the user on the display (26) or alternatively down-loaded to an external computer via a serial port (not shown).

More specifically, by the action of pushing the button the user powers up the entire unit, and causes the IMS cell 12 to be powered so as to detect negative ions. The first negative background reading is then automatically taken, following which the polarity of the cell 12 is reversed, to enable it to detect positive ions, and the procedure is repeated. On the subsequent actuation of the loudspeaker 40, a sample is drawn in through the pin-hole aperture 30 and, with the cell still powered to detect positive ions, a positive sample reading is taken. The polarity of the cell is then switched again, to enable it to detect negative ions, and a negative sample reading taken. Once the appropriate data have been stored in the memory, for future reference and analysis, the unit is automatically powered down. Since the entire procedure, between pressing the button and the unit powering itself down after having taken the appropriate readings, takes only about half a second, very little battery power is used. Accordingly the battery life is extremely long and that means that relatively small and light batteries may be used. This makes the unit more desirable for use as a portable gas detector.

In an alternative mode, it is possible for the user to instruct the device to take repeated measurements, say every ten minutes or so, without further user intervention. The resultant data may automatically be transferred via the serial port (not shown) to a remote recording and/or analysing computer. Used in this way, the present embodiment provides a very compact remote sensing device.

The information provided by the unit may be relatively simple (for example merely a determination that a particular sample to be detected is or is not present), but may also be considerably more complex. The output of the IMS cell 12, on each positive or negative measurement, may comprise a detailed spectrum. In the latter case, subtraction of the negative and positive background spectra from the negative and positive sample spectra provides the user with very detailed information by way of corrected negative and positive sample spectra, these corrected spectra being essentially independent of any contaminants that were inside the case 10 when the negative and positive background spectra were being taken. In this way, the unit automatically corrects for small traces of contaminants that might have been left over from the previous sample.

It will be appreciated that IMS equipment constructed in accordance with the invention requires no external dry air source nor a pumped internal closed-loop dry air circulatory system.

Dispensing with the need for an internal pump immediately reduces the power needed to be drawn from the instrument's internal low voltage cells, enabling smaller and lighter cells to be employed to power the instrument. Removing the need for a circulatory system simplifies the internal design of the equipment.

The equipment may thus be considerably reduced in volume and weight to the point where body-worn IMS equipment becomes feasible, even using present generation IMS cells and processing and control circuitry.

Further advantages arise from the use of IMS equipment the subject of the present invention. For example the presence of the molecular sieve material 14 inside the case 10 ensures that not only water-vapour but many potentially-contaminating organic vapours are absorbed whilst the equipment is out of use, for example in storage, or whilst in operational use but when not deployed, permitting rapid start-up without the need for any preliminary scouring or cleansing as is required in prior art equipment.

Rapid start-up and operation in turn means that power supplies can be further conserved or reduced in capacity as the equipment does not need to be kept continuously running between operations.

The simpler construction permitted by use of the present invention obviating the need for external dry air supplies or internal air circulation and drying systems also means that equipment in accordance with the invention is considerably cheaper to manufacture than prior art IMS equipment.

Figure 4:
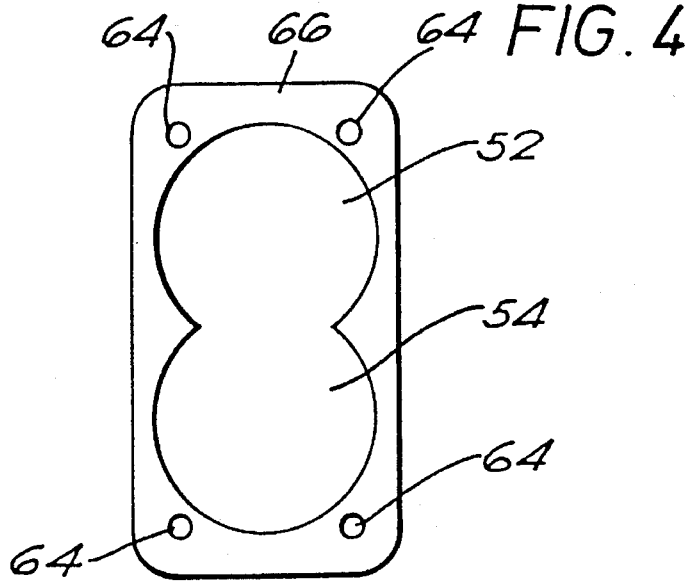
FIG. 4 shows an end view of the embodiment of FIG. 2, looking in the direction of the arrow IV of FIG. 2, with the end closure removed.
Figure 2:
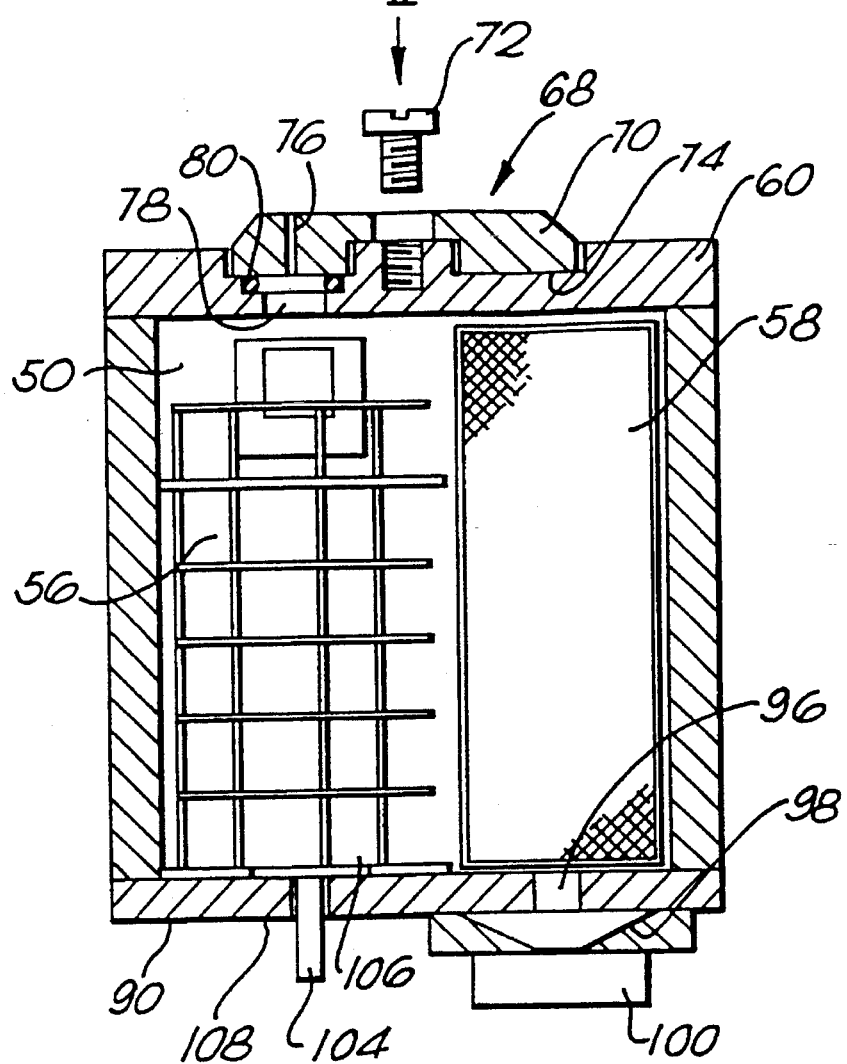
FIG. 2 is a cross-sectional view illustrating more specifically the construction and layout of part of a preferred embodiment of an IMS instrument.
Figure 3:
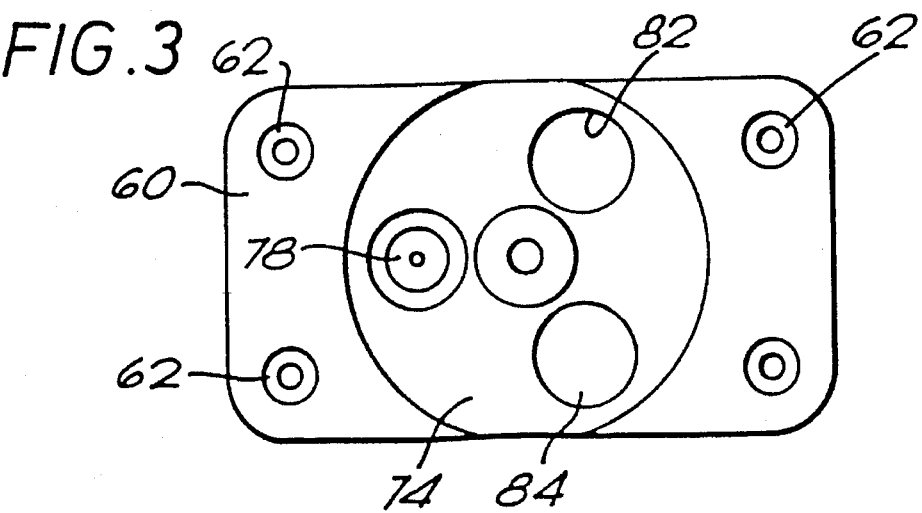
FIG. 3 is a plan view of part of the embodiment of FIG. 2.

Referring to FIGS. 2, 3 and 4 which show various aspects of a practical realisation of an IMS instrument in accordance with a preferred embodiment of the invention, a main body case 50, machined from a solid block of aluminium alloy, contains longitudinal bores 52 and 54 in which are mounted respectively an IMS cell 56 and a cylindrical gauze-walled container 58 packed with molecular-sieve drying agent.

The casing 50 is sealed at one end by a closure plate 60 mounted upon the end face of the casing 50 by means of screws which pass through holes 62 and engage in tapped bores 64 in the end face 66 of the casing 50. The closure plate 60 carries a shutter assembly 68 comprising a circular plate 70 mounted by means of a screw 72 to engage and rotate in an annular counterbore 74 upon the closure plate 60, either to align a pin-hole aperture 76 in the plate 70 with a port 78 or to close the port 78. An 'O' ring seal 80 seated in the port 78 maintains a seal between the prot 78 and the rear face of the shutter plate 70. Blind bores 82 and 84 in the closure plate 60 contain dummy 'O' rings seals to provide a three-point support for rotating plate 70.

At its other end, the casing 50 is closed by a closure plate 90, provided with an aperture 96. The aperture 96 which gives access to the interior of the casing 50 communicates with the inner face of a cone 98 of a miniature loudspeaker 100, mounted in sealed relationship upon the outer face of the closure plate 90.

A connector stem 104 of a collector electrode 106 of the IMS cell 56 protrudes through a hermetically-sealed and electrically insulated aperture 108 in the closure plate 90.

A housing, not shown, which may be a rearward extension of the casing 50, but which does not need to be sealed, contains a power supply unit for the instrument, primary or secondary cells for powering the power supply, instrument control and signal-processing circuits and a display module for indicating the presence and/or concentration of gases or vapours of interest in incoming samples.

To operate the instrument, the circular plate 70 is rotated by hand to align the pinhole aperture 76 with the port 78, so providing communication between the ambient atmosphere and the interior of the casing 50.

With power applied to the power supply unit from the primary or secondary cells, the IMS cell 56 and control and processing circuits are energised and the loudspeaker 100 may be operated under the control of the user and at a pre-determined rate to draw pulses of ambient atmosphere in through the pinhole aperture 76 and port the 78 into the entry port of IMS cell 56, where components of the sample are ionised and the resulting ions passed into the drift region of the cell 56 for separation and collection in a known manner.

Using the physical construction described in relation to FIGS. 2, 3 and 4, a self-contained IMS personal vapour detector with dimensions approximately 150 mm long, 60 mm wide and 35 mm deep has been realised and demonstrated.

It will be apparent to those skilled in the art that various modifications and variations can be made to the IMS equipment described herein without departing from the scope of the invention.

I claim:

1. IMS equipment comprising a hermetically sealed compartment containing an IMS cell and a body of absorbent material, sample means for introducing a sample into the compartment via an inlet thereof, the IMS cell being arranged to detect or identify gases or vapours of interest present in the sample, water vapour or other interfering species introduced into or otherwise present within the compartment diffusing within the compartment and being absorbed by the body of absorbent material.

2. IMS equipment as claimed in claim 1 in which the sampling means comprises pressure-pulse means arranged to create a negative pressure pulse within the compartment, thereby drawing in the sample via the inlet.

3. IMS equipment as claimed in claim 2 in which the pressure-pulse means comprises a transducer.

4. IMS equipment as claimed in claim 2 in which the pressure-pulse means comprises a loudspeaker.

5. IMS equipment as claimed in any one of the preceding claims in which the body of absorbent material comprises a molecular sieve material.

6. IMS equipment as claimed in claim 1 in which the inlet comprises a pinhole aperture in a wall of the compartment.

7. IMS equipment as claimed in claim 6 including sealing means for sealing the pinhole aperture when the equipment is not in use.

8. IMS equipment as claimed in claim 1 including electronic control means arranged to actuate the IMS cell to take a reference measurement prior to actuation of the sample means and the resultant introduction of the sample into the compartment.

9. IMS equipment as claimed in claim 8 including analysis means arranged to subtract the reference measurement from a sample measurement to provide a corrected sample measurement.

10. IMS equipment as claimed in claim 8 or claim 9 in which the electronic control means are arranged to actuate the IMS cell to take a first reference measurement, by detection of ions of one charge, then a second reference measurement by detection of ions of the opposite charge, both prior to actuation of the sample means and the resultant introduction of the sample into the compartment.

11. IMS equipment as claimed in claim 8 in which the electronic control means are arranged to actuate the IMS cell to take a first sample measurement, after actuation of the sample means and the resultant introduction of the sample into the compartment, by detection of ions of one charge, and then to take a second sample measurement by detection of ions of the opposite charge.

12. IMS equipment as claimed in claim 1 in which the output of the IMS cell is a detected spectrum, the spectrum being stored in computer memory.

13. IMS equipment as claimed in claim 12 including input/output means for interrogating the computer memory via an external link.

14. IMS equipment as claimed in claim 1 including manual or electric actuation means arranged, when actuated by a user of the IMS equipment, automatically to power up the IMS cell, to activate the sample means thereby introducing a sample into the compartment, to cause the IMS cell to take a measurement of the sample, and to power down the cell, all without further user intervention.

15. IMS equipment as claimed in claim 1 in which the compartment at least partially comprises a block of material, the IMS cell and the absorbent material being contained within respective parallel bores within the block.

\* \* \* \* \*